United States Patent
Avihod

[11] Patent Number: 5,256,135
[45] Date of Patent: Oct. 26, 1993

[54] THORACIC-LUMBAR-SACRAL CORRECTIVE ORTHOSIS ("TLSO") CORRECTIVE BACK SUPPORTING BRACE AND CHAIR SIDE SUPPORT BUTTRESS

[75] Inventor: Eli Avihod, Studio City, Calif.

[73] Assignee: Medisol U.S.A., Inc., South El Monte, Calif.

[21] Appl. No.: 825,648

[22] Filed: Jan. 23, 1992

[51] Int. Cl.$^5$ .......................... A61F 5/00; A61F 5/37
[52] U.S. Cl. ...................................... 602/19; 128/874
[58] Field of Search ............... 128/874, 875, DIG. 15, 128/96.1, 78, 102.1, 75, 100.1, 84, 99.1; 602/5, 18, 19; 2/44, 102, 92

[56] References Cited

U.S. PATENT DOCUMENTS

| | | | |
|---|---|---|---|
| 94,087 | 8/1864 | Dike | 602/19 |
| 470,839 | 3/1892 | Klem | 602/19 |
| 945,359 | 1/1910 | Adams | 602/19 |
| 1,070,067 | 8/1913 | Robinson | 602/19 |
| 1,075,348 | 10/1913 | Fritsch | 602/19 |
| 2,632,178 | 3/1953 | Kennedy | 602/19 |
| 3,362,402 | 1/1968 | Loeffel | 602/19 |
| 3,543,748 | 12/1970 | Charters | 602/19 |
| 4,143,654 | 3/1979 | Sherman | 602/19 |
| 4,794,917 | 1/1989 | O'Leary | 602/18 |
| 5,007,412 | 4/1991 | Dewall | 602/19 |

Primary Examiner—Michael A. Brown

[57] ABSTRACT

A thoracic-lumbar-sacral corrective orthosis ("TLSO") device, for supporting, controlling and correcting structural and postural curvature and deformation of the spine and a chair side support buttress to further support a patient seated in a chair. The TLSO device can be used by ambulatory and non-ambulatory patient's alike and has an arcuate rigid back portion, a flexible vest portion and straps to hold the TLSO device against the patient's back to apply corrective pressure to the patient's spine. A lumbar support cushion is located on the arcuate rigid back portion to provide lumbar support to the patient's spine. Chair attachment straps are affixed to arcuate rigid back portion for use in securing a patient wearing the TLSO device in a chair. The chair side support buttress is positioned between the armrest of a chair and extends upwards to lie adjacent to the patient's side. An underarm cut-out region permits the patient's arm to be looped over the upper region thereby assisting the patient in sitting properly in a chair, rather than slumping forwards or to one or both sides.

18 Claims, 5 Drawing Sheets

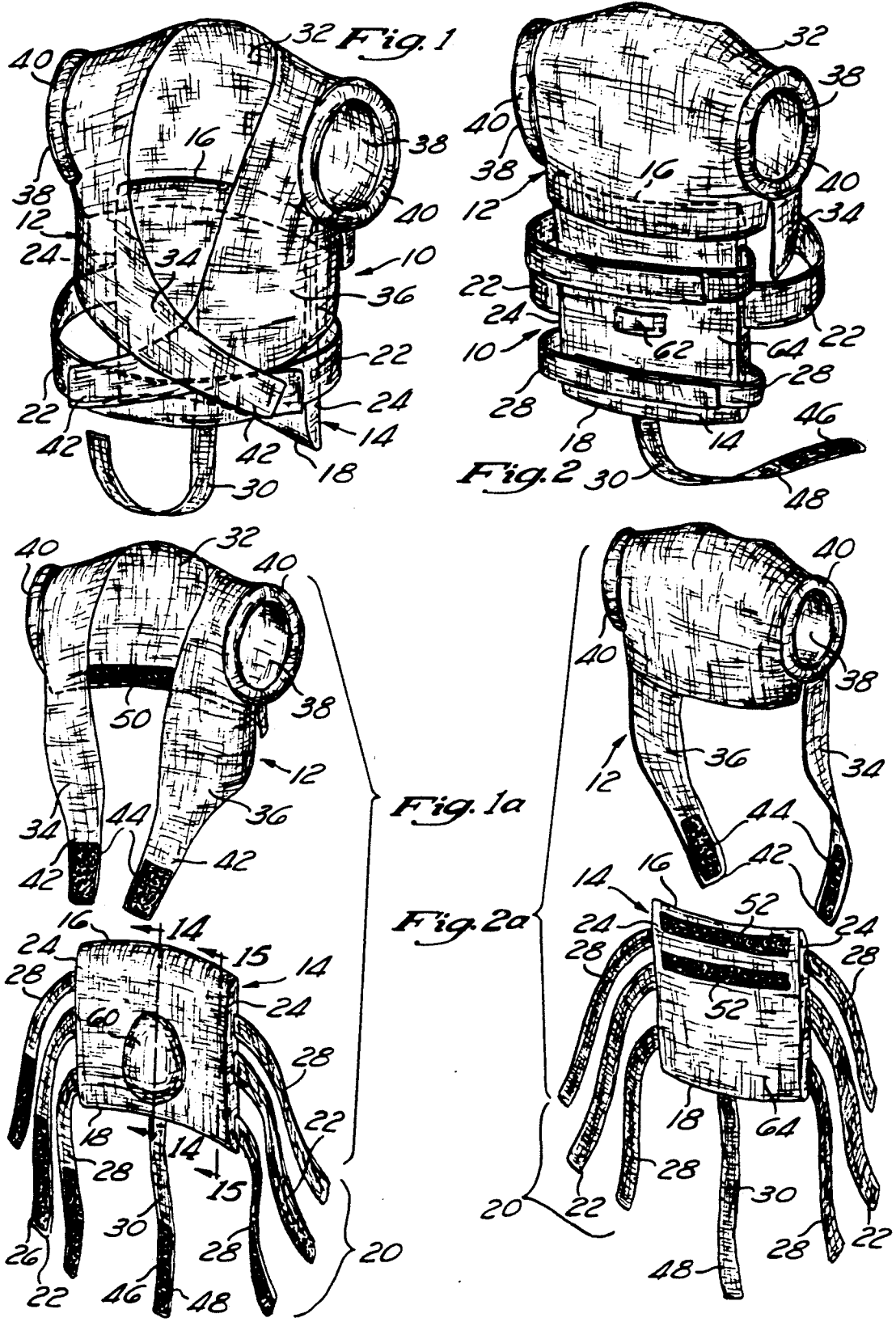

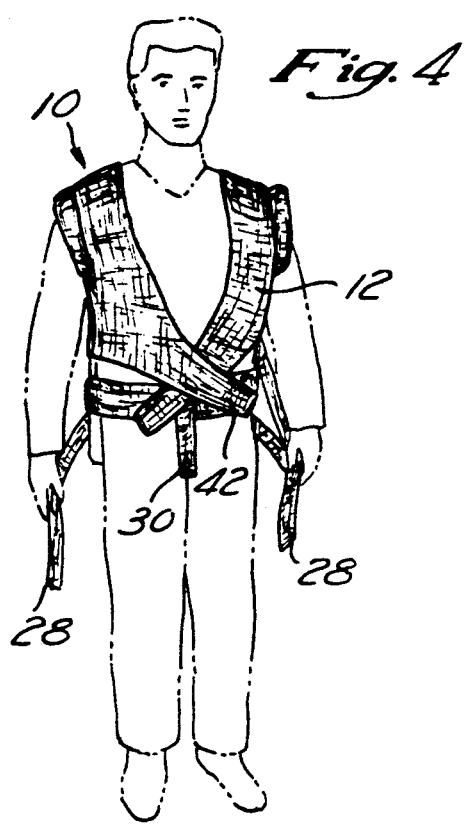
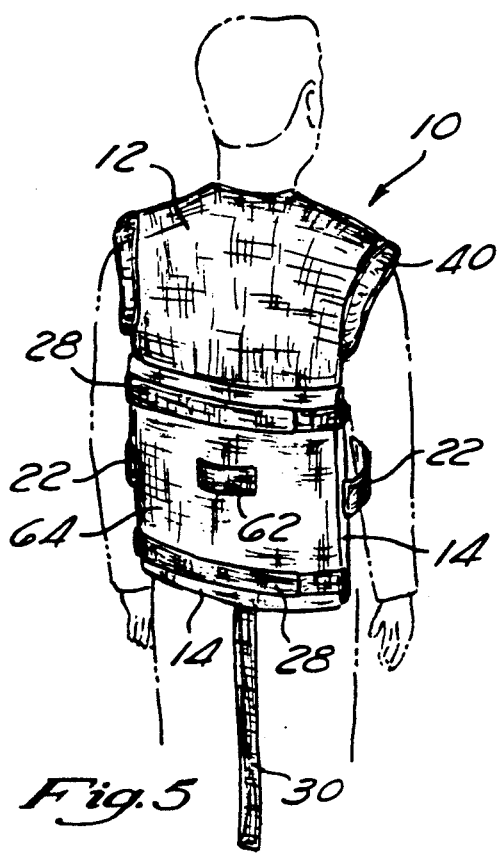
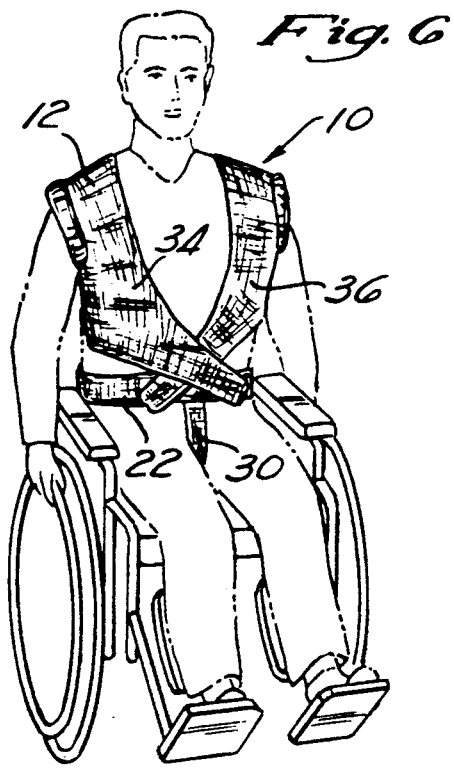
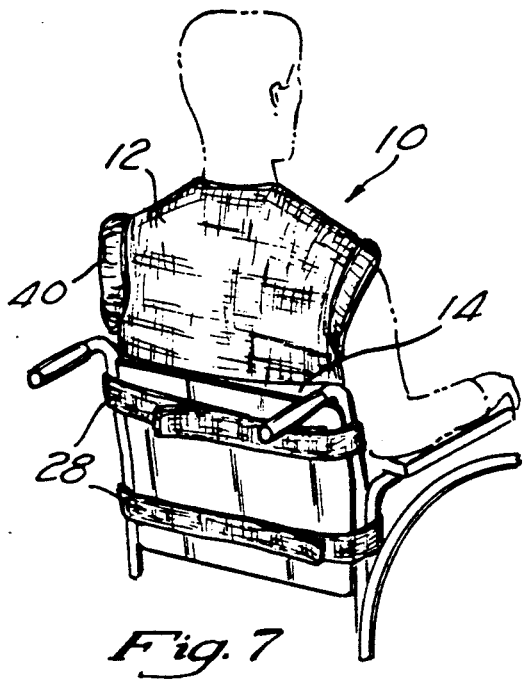

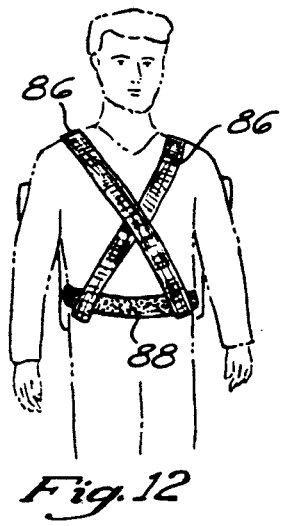
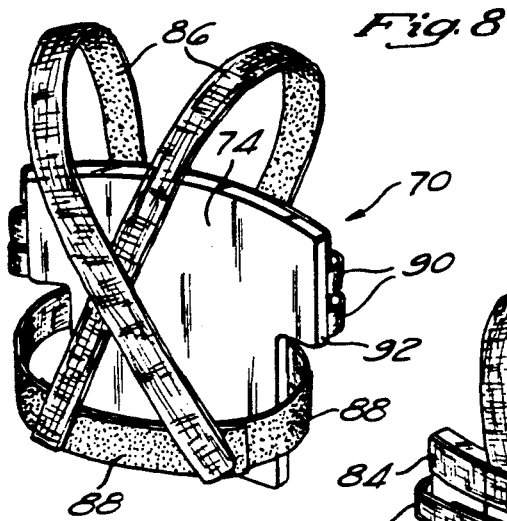
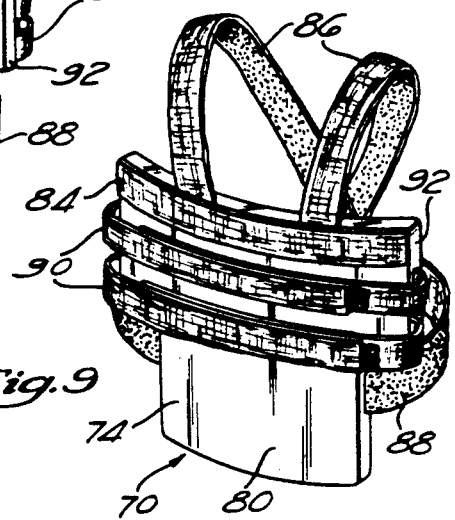
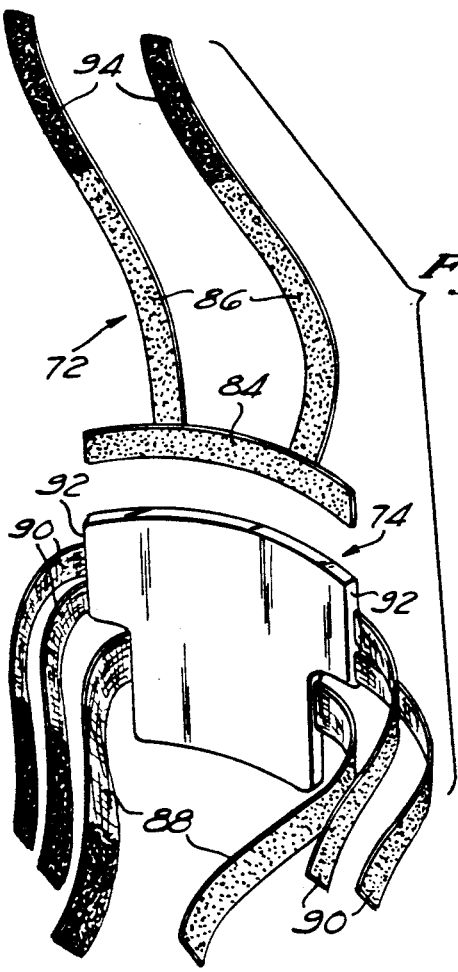
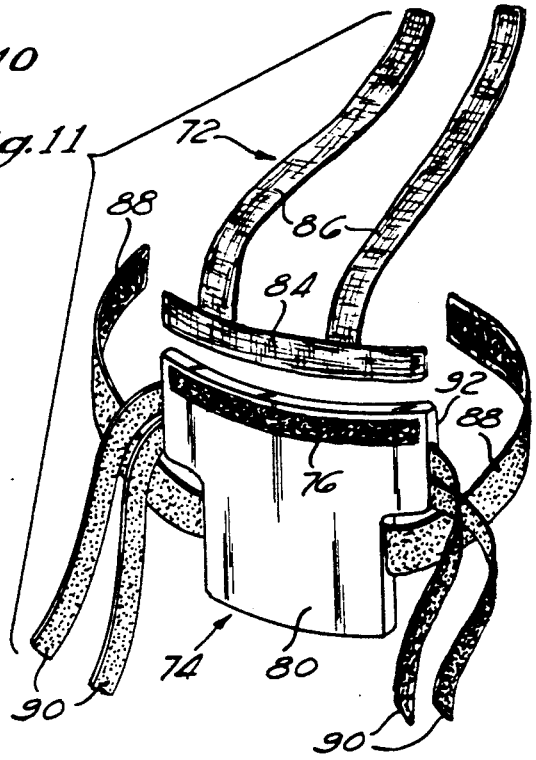

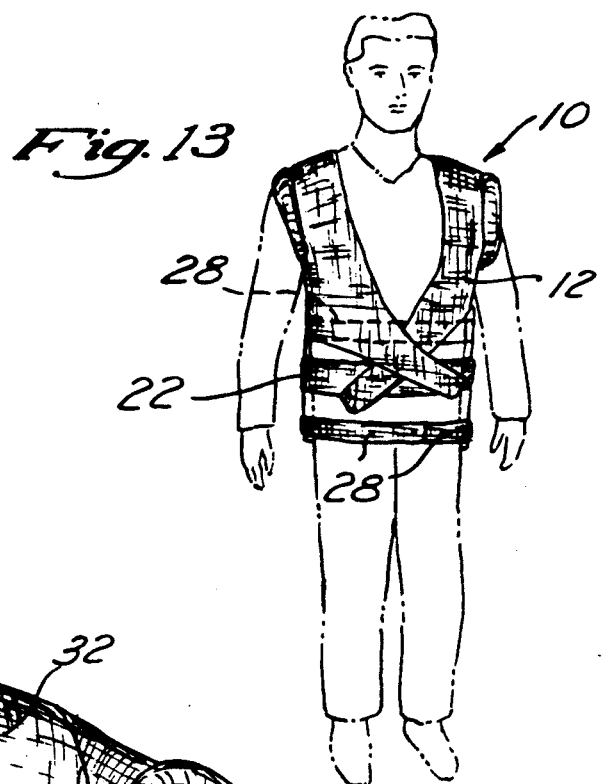
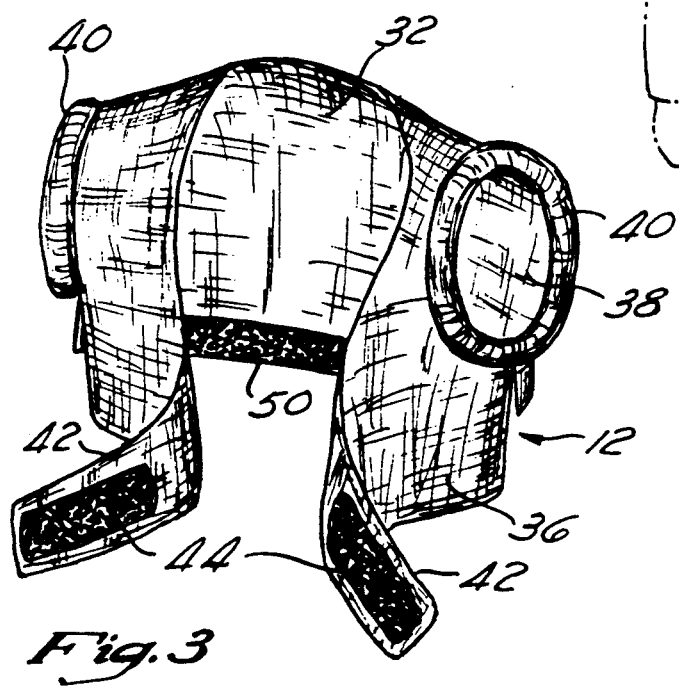
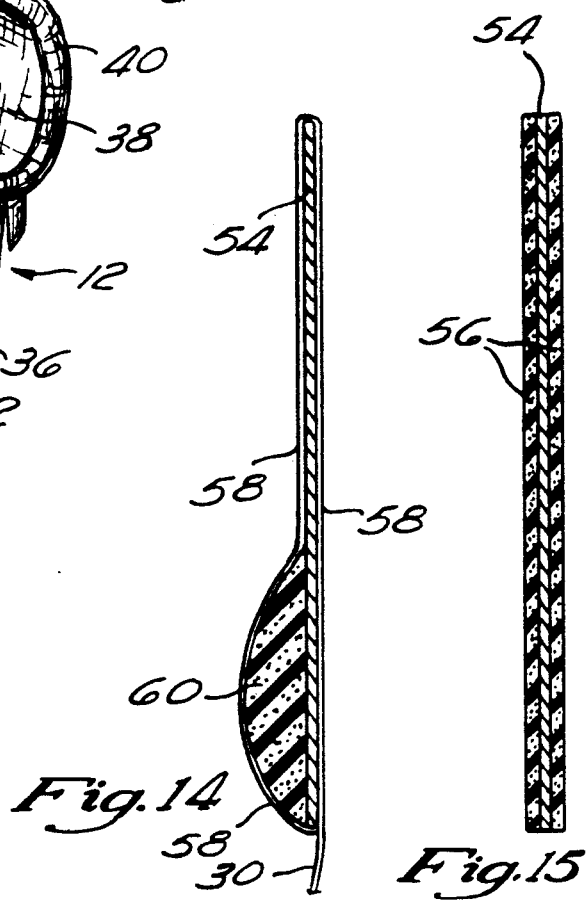

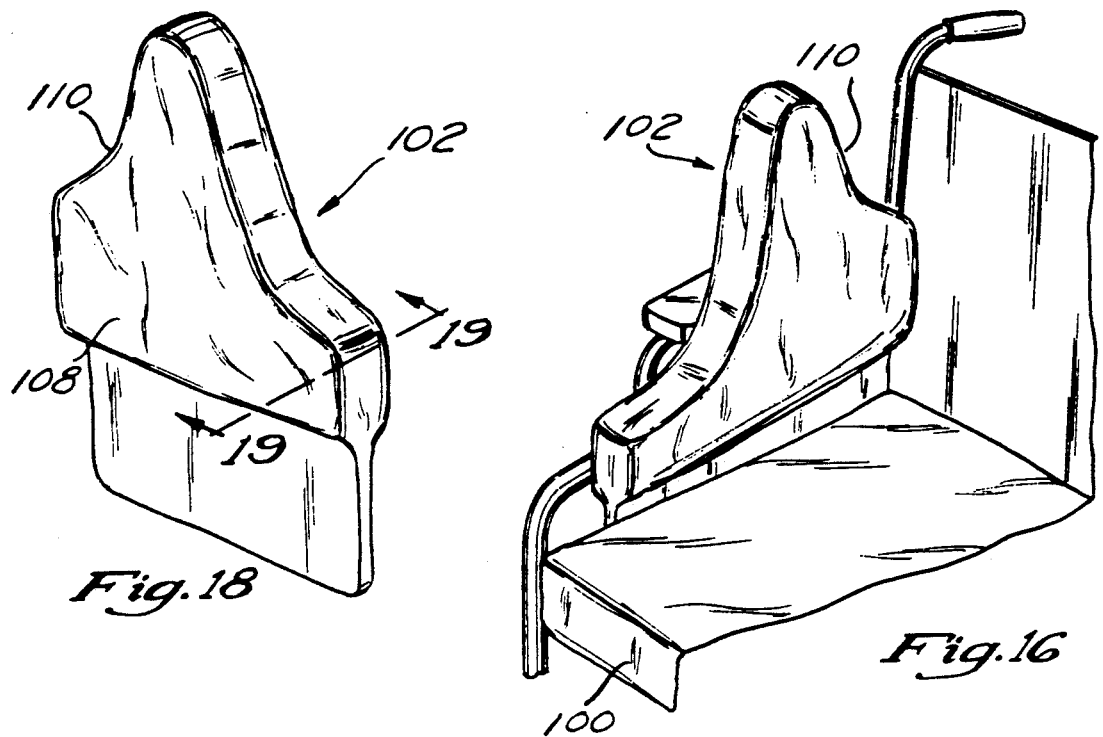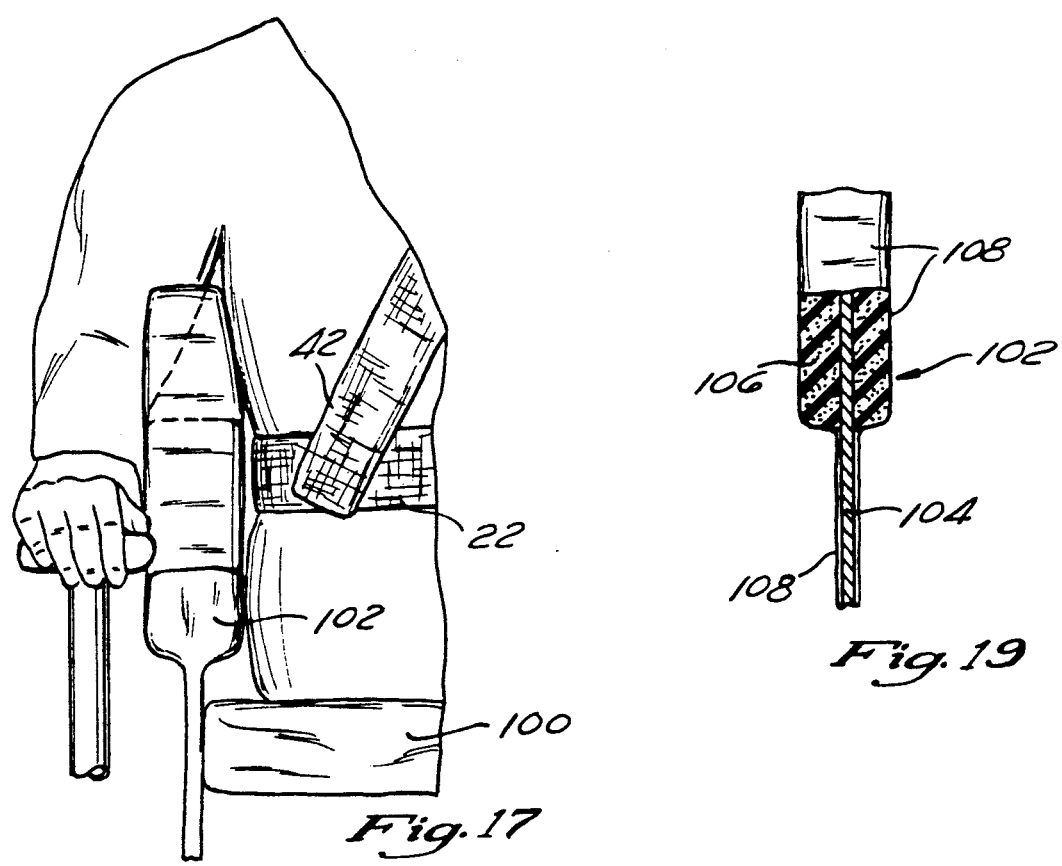

5,256,135

THORACIC-LUMBAR-SACRAL CORRECTIVE ORTHOSIS ("TLSO") CORRECTIVE BACK SUPPORTING BRACE AND CHAIR SIDE SUPPORT BUTTRESS

BACKGROUND OF THE INVENTION

1. Field of the Invention

The invention relates to the field of Thoracic-lumbar-sacral corrective orthosis, known by its acronym "TLSO", for supporting, controlling and correcting poor structural and postural curvature and deformities of the spine, and more particularly for TLSO devices which can be worn by ambulatory and non-ambulatory patients when they are in or out of a seat, on a bed, and the like and which provides a means to conveniently and comfortably secure a patient in a wheelchair when desired.

2. Description of the Prior Art

There are numerous devices available to aid in stabilizing the spine and back of a patient.

In the U.S. Pat. No. 4,898,185 to Fuller, the brace has a back portion with two waist straps which wrap around the patient's waist. The back portion has one layer of Velcro ® hook and loop attachment material to hook onto complementary Velcro ® attachment material which is fixed to the back of a chair or wheelchair. However, the Fuller device lacks a lumbar support pad, does not adequately support the patient's spine, and does not allow for gradual correction.

U.S. Pat. No. 4,050,737 to Jordan discloses a support harness for use for children lacking trunk or head control to achieve and maintain a normal sitting position. However, as with the Fuller device, the Jordan device does not provide the proper contour for a patient's back in that it teaches using either no back board or a straight back board, and also does it provide for necessary lumbar support.

U.S. Pat. No. 5,076,264 to Lonardo, et al. teaches a medical appliance for treating spinal conditions. However, the appliance disclosed is bulky and significantly constricts the patient's freedom of movement.

The prior art devices are all relatively inconvenient to use and uncomfortable for the patient to wear. For example, when a patient wearing a device which lacks adequate back support is seated in a soft chair or wheelchair (having pliable backs), the patient's back will tend to bend and arch further out of correct alignment, thus causing discomfort or pain to the patient. This problem is acute for patient's who are seated in foldable wheelchair with flexible backs and seats which tend to hammock when a patient is seated. For patient's using prior art TLSO devices, the hammocking effects are particularly problematic and interfere with the manipulation a corrective effects sought to be achieved by using these TLSO devices.

Additionally, the prior art devices provide no convenient way to gradually correct and improve defects in the patient's spinal curvature and posture. Lastly, with the prior art devices, there is truly no effective way to comfortably, yet securely, prevent a seated patient wearing such devices from slouching or slumping forward or to one or both sides.

SUMMARY OF THE INVENTION

The invention disclosed herein solves the problems outlined above by providing a unique and novel TLSO back brace with a rigid arcuate back brace portion with a lumbar support cushion, a number of attachment straps, and a fabric vest or suspender portion attached to the arcuate rigid back brace portion. The patient wears the vest portion and its attached rigid back brace portion by passing his or her arms through the arm holes of the vest or wrapping its suspender straps over his or her shoulders, wrapping the waist strap snugly around his or her waist, looping the crotch strap affixed to the bottom of the rigid back brace portion forwardly between the patient's legs and attaching it to the front of the waist strap secured around the patient's waist, and finally, engaging the chest panels of the vest or suspender straps to the waist strap. Worn as such, the TLSO device will snugly, yet securely fit to the patient's back, thereby applying corrective pressure to the spine to support and correct deficiencies and defects in the spine. By adjusting the straps, the vest panels, the size of the arcuate back portion, and the size, shape and density of the material of the lumbar support cushion, the TLSO device of the invention can be conveniently used to affect step-by-step changes in a patient's posture and spinal position.

For chair or wheelchair use, the patient wearing the device is seated in a chair or wheelchair, and straps affixed to the side edges of the rigid back portion can be wrapped around the rear seat back of the wheelchair and affixed together, thereby preventing the patient wearing the device from slumping forward or from side to side. For patients who tend to fall to one or both sides of a chair, an accessory side support buttress of the invention may be snugly positioned between the side of the chair and an accessory seat cushion placed on the seat of the chair, or the accessory side support buttress can be otherwise fixed adjacent to the side of the wheelchair.

One major aspect of this invention thus comprises a thoracic-lumbar-sacral corrective orthosis brace for supporting, controlling and correcting poor structural and postural curvatures and deformations of the spine of a patient wearing the brace, comprising:

an arcuate rigid back portion having a top and bottom regions, two side regions and a front and rear facing surface, said rigid back portion being curved rearwardly from said two side regions away from the patient's back; and a flexible vest portion, said vest portion being attached to said arcuate rigid back portions, said arcuate rigid back portion and said flexible vest portion having means with which to hold said arcuate rigid back portion against the patient's back to apply controlling and corrective pressure to the patient's spine.

Another aspect of the invention comprises a thoracic-lumbar-sacral corrective orthosis brace for supporting, controlling and correcting poor structural and postural curvature and deformities of the spine of a patient wearing the brace, comprising:

a concave rigid back portion having a top and bottom regions, two side having a top and bottom regions, two side regions and a front and rear facing surface, said rigid back being concavely curved rearwardly from said two side regions away from the patient's back;

a flexible vest portion which is detachably affixed to said concave rigid back portion near its top region, said concave rigid back portion having rigid back portion straps originating from its side regions, said rigid back portion straps comprising at least one waist strap which can be used to adjustably and detachably strap said concave rigid back portion to the patient's back and at least one chair engaging strap for use to adjustably and detachably secure the concave rigid back portion to a chair, and at least one strap originating from said bottom region of said concave rigid back portion which can be passed forwardly between the patient's legs and adjustably and detachably affixed to said waist strap wrapped around the patient's waist, said flexible vest portion being worn on the patient's upper torso and having chest overlaying portions which can be adjustably and detachably affixed to said waist strap wrapped around the patient's waist; and a lumbar support cushion located on said front facing surface of said concave rigid back portion, said lumbar support cushion being available in a variety of shapes, sizes and densities, wherein said brace is thus capable of being adjusted to fit the patient's torso and spinal conditions as required.

A third aspect of the invention comprises a chair side support buttress for use with a chair by a patient who requires support to prevent the patient from slumping sideways or forwards in a chair, comprising:

a side support unit having an upper region and a lower region, said side support unit being padded at it upper region and having a cut-out area at its upper rear portion and an elevated portion forward of said cut-out portion;

said side support unit having mean to position it adjacent to a side region of the chair, wherein in use, the patient is seated in the wheelchair such that the patient's underarm is placed over said cut-out area with said raised portion being positioned in front of the patient's under arm, thereby preventing the patient from slumping sideways or forward.

BRIEF DESCRIPTION OF THE DRAWINGS

FIG. 1 is a front perspective view of a first embodiment of the TLSO device.

FIG. 1a is an exploded view of FIG. 1 showing the two main portions of the TLSO device.

FIG. 2 is rear perspective view of the TLSO device shown in FIG. 1.

FIG. 2a is an exploded view of FIG. 2.

FIG. 3 is a front perspective view showing the vest portion of the TLSO device.

FIG. 4 is a view of a standing patient partially wearing the TLSO device.

FIG. 5 is a rear view of a standing patient partially wearing the TLSO device.

FIG. 6 is a front view of a patient wearing the TLSO device seated in a wheelchair.

FIG. 7 is a rear view of patient wearing the TLSO device seated and strapped in a wheelchair.

FIG. 8 is a front perspective view of the second embodiment of the TLSO device.

FIG. 9 is a rear view of the second embodiment of the invention.

FIG. 10 is an exploded view of FIG. 8.

FIG. 11 is an exploded view of FIG. 9.

FIG. 12 is a front perspective view of patient wearing the second embodiment of the TLSO device.

FIG. 13 is a front perspective view of a patient wearing the first embodiment of the device with the seating attachment straps being used to wrap around the patient's torso.

FIG. 14 is a cross-sectional view of the arcuate rigid back portion of FIG. 1a through view lines 14—14 showing the lumbar support cushion.

FIG. 15 is a cross-sectional view of the arcuate rigid back portion of FIG. 1a through view lines 15—15.

FIG. 16 is a perspective view of the side support buttress of the invention positioned in a wheelchair.

FIG. 17 is a front view of the side support cushion positioned in a wheelchair being used by a seated patient.

FIG. 18 is a front perspective view of the side support cushion of the invention.

FIG. 19 is a cross-sectional view of the side support cushion of FIG. 18 through view lines 19—19.

DETAILED DESCRIPTION OF THE DRAWINGS

As shown in FIGS. 1, 1a, 2, 2a and 3, a first embodiment of the TLSO device is illustrated. The TLSO device 10 has a vest portion 12 affixed to a concave rigid back portion 14 at or near its top edge 16. The curved rigid back portion 14 is curved concavely along its entire length from its top edge 16 to its bottom edge 18 and is curved backwardly from the sides 24 of the rigid back portion 14, away from the patient's back to fit the contour of a patient's back. This feature is extremely important from a comfort standpoint since a straight back portion will improperly cradle the patient's back, and will thus interfere with the corrective and supportive functions of the TLSO device.

Two or more pairs of attachment straps 20 are affixed to the rigid back portion 14. A first pair of attachment strap 20 are waist straps 22 for wrapping around the patient's waist. The waist straps 22 are positioned at approximately midway between the top edge 16 and the bottom edge 18 of the curved rigid back portion and extend outwardly from the sides 24 of the curved rigid back portion 14.

The waist straps 22 have means to detachably but fixably engage each other together, such as Velcro ® 26 hook and loop type attachment material, snaps, buckles, clips, clamps, or other known attachment means to allow the waist straps 22 to be adjusted to snugly and securely wrap around the patient's waist. It is understood that any known attachment means can be employed. At least one pair of seating restraining straps 28 are affixed to extend from the sides 24 of the curved rigid back portion 14. The restraining straps 28, as well as the waist straps 22 can be permanently affixed, such as by sewing, or can be made to be removable by hooks, snaps, clips, buttons, Velcro ®, or other known means (not shown). In FIG. 1, 1a, 2, 2a, and 3-6, two pairs of restraining straps 28 are shown, one pair each being affixed above and below the waist strap 22. Alternately, as shown in FIGS. 7-10, both restraining straps can be affixed to lie above the waist straps 22. The TLSO device 10 preferably also has a between-legs strap 30, the use of which will be described further below.

The vest portion 12 is made from flexible material such as fabric or mesh material and has a back 32 and two overlapping chest panels 34 and 36 extending from the sides of the back 34. Arm holes 38 are located at the interface of the back 34 and chest panels 36 through which the patient's arms pass through as is shown in FIGS. 3-6. For comfort, the arm holes 38 have a padded perimeter 40, with padding such a silicone fiber, polyester fiber, or other material. Silicone fiber is ideal since it resists bacterial and other pathogenic organism growth, is lightweight, and breathes well. The vest portion 12 is worn on the patient's upper torso.

The overlapping chest panels 36 are patterned so that in use, once the patient wears the TLSO device 10 by passing his or her arms through the arm holes 38 of the vest portion 12 and wrap and secures the waist straps 22 around the patient's waist, the end regions 42 of the overlapping chest panels 30 will overlay a portion of the waist straps 22 secured around the patient's waist. Chest panel-waist strap attachment means 44 are located on the end regions 42 of the overlapping chest panels 36 to permit same to be adjustably and detachably engaged with the waist strap 22 and each other to snugly, yet comfortably engage the upper portion of the TLSO device 10 with the patient's torso. The attachment means 44 can be Velcro® hook and loop type attachment material, snaps, buckles, clips, clamps or other known attachment means.

The between-leg strap 30 has between-leg strap-waist strap attachment means 46 located at its end region 48. After the patient's arms are passed through the arm holes 38 of the vest portion 12, and the waist strap 22 is secured around the patient's waist, the between-leg strap 30 is passed between the patient's legs and is looped around the front of the patient's torso and is adjustably and detachably engaged with a frontwardly facing portion of the waist strap 22. This assists in firmly pressing the bottom portion of rigid back portion 14 of the TLSO device 10 against the patient's lower back and also helps to prevent the TLSO device 10 from "riding" up the patient's back, thereby assisting in correcting the patient's posture and spine position. Also, if the patient being walked were to suddenly collapse at his or her knees, the between-leg strap 30 will allow the assistant to better prevent the patient from being injured. The between-leg strap—waist strap attachment means 42 can, like the other straps, comprise Velcro® hook and loop type material or other known attachment means.

As shown in FIGS. 1a and 1b, the vest portion 12 is preferably made to be detachably affixed to the arcuate rigid back portion 14 near its top edge 16. The vest portion 12 can have a first attachment means 50 position on the inside face of the back 34 of the vest 12 at or near it bottom edge 50. Complementary attachment means 52 are fixed to the rear side 64 of the rigid back portion 14 facing away from the patient's back. The attachment means 50 and 52 can conveniently consist of Velcro® hook and loop type attachment means, although it is contemplated that other known means such as hooks, snaps, buttons, clips, can also be used. For adjustability sake, the vest portion—rigid back portion attachment means can be arranged to allow the vest portion 12 to be selectably positioned at two or more positions on the rigid back portion 14. This can be conveniently accomplished by having a plurality of Velcro® strips 52 affixed to the rigid back portion, or utilized a Velcro® complementing strip 52 wider than that of the first Velcro® strip 50. An, additional advantage afforded by having the vest portion 12 detachably fixable to the arcuate rigid back portion 14 is that it allows any given arcuate rigid back portion 14 to be used with vest portion 12 having a desired size, color and pattern for perfect patient fit, matching with his or her wardrobe, and for ease of laundering. As previously noted, the attachment straps 20, can also be made to be detachably affixed to the arcuate rigid back portion 14 for selection of proper length, color and pattern, and also for ease of laundering and cleaning.

The arcuate rigid back portion 14 can be made from wood, plastic, metal or other suitable materials. FIGS. 14 and 15 are cross-sectional views through the arcuate rigid back portion 14 of FIG. 1a. The arcuate back portion 14 can be conveniently made from a multi-ply wood sheet which has been heat and pressure shaped to form the arcuate core 54, or alternately from molded plastic or shaped metal. The arcuate core 54 can be, but need not be overlain with a layer of foam or padding material 56 to give it extra cushion. The arcuate core 54 is then surrounded with an outer layer of vinyl or a fabric 58. The attachment straps 20, including the waist straps 22 and seating engagement straps 28, and between-legs strap 32 can be conveniently permanently attached to the edges of the rigid back portion 14 near the edges of the vinyl or fabric covering 28 by stitching or can be made detachably attachable (not shown).

As shown in FIGS. 1a and 14, the arcuate rigid back portion 14 receives a lumbar support cushion 60 between the side of the arcuate core 54 facing the patient's back and the covering material 58. The proper size, shape, density of material, and position of the lumbar support cushion 60 will be selected by the physician, chiropractor, or other health care professional fitting the patient with the TLSO device 10. After the proper lumbar support cushion 60 is selected and its proper position is determined, it can then be secured in place against the core 54, such as by Velcro® or by gluing. For ease of use, and for ready access to the lumbar support cushion 60, an access means such as a zipper or laced opening can be provided (not shown). In the event the health care professional does not desire that the patient or other unauthorized person disrupt the lumbar support cushion 60, access to the lumbar support cushion 60 can be made inconvenient by sewing or otherwise permanently securing the covering 58 completely around the arcuate core 54.

As described above, and as shown in FIGS. 6 and 7, a patient wearing the TLSO device 10 can be strapped to a regular chair or a wheelchair by tightly wrapping the adjustable seating restraining straps 28 around the back of the chair's back and detachably engaging them together to thereby prevent the patient from shifting from side-to-side in the chair or from slumping forward.

If the patient is ambulatory, the seating attachment straps 28 can be attached together at the back side 64 of the arcuate rigid back portion 14 so that they do not flop loosely, and the patient can be assisted in walking by a helper or nurse by grasping one or both pairs of the seating attachment straps which are attached together, as shown in FIG. 5. A grasping strap 62 can also be affixed to the back side 64 of the arcuate rigid back portion 14 to aid patient assistants in help walking the patient.

As shown in FIG. 13, one or both of the seat supporting strap 28 can alternately be wrapped forwardly around the patient's chest and lower torso to provide additional pressure to force the curved rigid back portion 14 of the TLSO device 10 more tightly against the patient's back.

FIGS. 8–12 illustrates a second embodiment of the TLSO device 70 wherein a suspender portion 72 can be detachably affixed to the lower arcuate rigid back portion 74 with attachment means 76 and 78 located on the upper region of the back surface 80 of the curved rigid lower back portion 74 and a suspender support strip 84, respectively. The suspender support strip 84 has two suspender straps 86 affixed thereto. As with the first embodiment, a pair of waist straps 88 and seating attachment straps 90 are fixed on the sides 92 of the lower arcuate rigid back portion 74. FIG. 12 depicts a patient wearing the TLSO device 70 The waist straps 88 are snugly wrapped around the waist of the patient and its suspender straps 86 are crisscrossed over the patient's chest and detachably affixed to the waist strap 88 with Velcro ®, hook and loop type material 94 sewn to the end regions of the suspender straps 86 and on the outer surface of the waist straps 96.

The arcuate rigid back portions 14 and 74 of either embodiment can be provided in a series of widths and lengths to best fit the patient. For example, the width of the arcuate rigid back portion from side to side can be 14, 16 or 18 inches and the length can be 15, 17 or 19 inches. These ranges will to accommodate the needs of most adult patients. Ideally, for maximum support, the upper edge 16 of the arcuate rigid back portion 14 should be as least as high as the number five dorsal vertebra when the TLSO device is properly worn, although it can extend higher or slightly lower relative to the number five dorsal vertebra.

When a patient wearing the TLSO device 10 or 70 is seated in a conventional chair with armrests or a wheelchair, the TLSO device can be conveniently used with an accessory seat cushion 100 and a side support buttress 102 shown in FIGS. 16-19. The accessory seat cushion 100 can be made to be relatively stiff or soft, as the need arises. For example, for use with foldable wheelchairs, which generally have flexible vinyl seats, it is preferable that the accessory seat cushion 100 be firm.

The side support buttress 102 is positioned between the armrest side of a conventional chair or wheelchair and the side wall of the accessory cushion 100. As shown in FIG. 19, which is a cross-sectional view of the side support buttress 102, the side support buttress 102 has a central stiff board 104, a foam layer 106 which covers the upper region of the stiff board 104, and has a fabric or vinyl covering 108 which surrounds the foam layer 106 and the stiff board 104. The absence of a foam layer 106 covering the lower portion of the stiff board 104 allows the side support buttress 102 to be slid between the side of the accessory cushion 100 and the side of the wheelchair and tightly positioned therebetween. The side support buttress 102 has a arm support cut-out 110 which the patient places under the hollow of his or her arm, thus providing additional support for the patient who tends to slump forward or to one or both sides. In the event the patient does not require the TLSO device 10 or 70 of the invention, but nevertheless needs side support in a chair with armrests or a wheelchair, the side support buttress 102 can be used alone, or in pairs. The side support buttress 102 can alternately be made solely of dense foam, plastic, or other materials, if desired, and can also be positioned in a chair relative to the patient's underarm by other known means.

The drawings and the foregoing description are not intended to represent the only form of the invention in regard to the details of its construction and manner of operation. In fact, it will be evident to one skilled in the art that modifications and variations may be made without departing from the spirit and scope of the invention. Changes in form and in the proportion of parts, as well as the substitution of equivalents, are contemplated and although specific terms have been employed, they are intended in a generic and descriptive sense only and not for the purpose of limitation, the scope of the invention being delineated in the following claims:

I claim:

1. A thoracic-lumbar-sacral corrective orthosis brace for supporting, controlling and correcting poor structural and postural curvature and deformations of the spine of a patient wearing the brace, comprising:
   a unitary, rigid back portion which arcuately extends between its top and bottom edges, and two side edges having a front and rear facing surface, said rigid back portion being curved generally rearwardly from said two side edges away from the patient's back said portion substantially overlying the patient's back, said top edge lying in the vicinity of the number five thoracic vertebra and said bottom edge lying in the vicinity of the sacrum; and
   a flexible vest portion, said vest portion attached to said unitary, rigid back portion, said rigid back portion and said flexible vest portion having strap means affixed thereto with which to hold said rigid back portion against the patient's torso and back to apply controlling and corrective pressure to the patient's spine between the vicinity of the number five thoracic vertebra and the sacrum.

2. The thoracic-lumbar-sacral corrective orthosis brace of claim 1, wherein said rigid back portion further comprises a lumbar support protrusion which is located on said front facing surface, said lumbar support protrusion being sized to impart additional controlling and corrective pressure to the patient's spine.

3. The thoracic-lumbar-sacral corrective orthosis brace of claim 2, wherein said lumbar support protrusion comprises a cushion which can be fixed to the front facing surface of said rigid back portion.

4. The thoracic-lumbar-sacral corrective orthosis brace of claim 3, wherein said cushion is provided in a variety of shapes, sizes, and hardness.

5. The thoracic-lumbar-sacral corrective orthosis brace of claim 3, wherein said cushion can be detachably affixed on said front facing surface of said rigid back portion.

6. The thoracic-lumbar-sacral corrective orthosis brace of claim 1, wherein said flexible vest portion is detachably fixable to said rigid back portion.

7. The thoracic-lumbar-sacral corrective orthosis brace of claim 1, wherein said strap means comprises at least one waist strap to be wrapped around the patient's torso and at least one portion of said flexible vest portion which can be detachably engaged with said at least one waist strap.

8. The thoracic-lumbar-sacral corrective orthosis brace of claim 7, wherein said flexible vest portion comprises a back panel with two chest panels extending from said back panel, said chest panels being crossable over the patient's chest and having portion which are detachably engageable with said at least one waist strap wrapped around the patient's waist.

9. The thoracic-lumbar-sacral corrective orthosis brace of claim 7, wherein said vest portion comprises a pair of shoulder straps which extend upwardly from said rigid back portion and which can be passed over the patient's shoulders and crossed over the patient's chest and detachably secured to said at least one waist strap wrapped around the patient's torso.

10. The thoracic-lumbar-sacral corrective orthosis brace of claim 7, wherein said strap means are detachably engageable to each other by at least one of hook and loop materials, straps, buckles, or clips.

11. The thoracic-lumbar-sacral corrective orthosis brace of claim 7, wherein said strap means further comprises a between-legs strap which is affixed and extends from said bottom edges of said rigid back portion, and which can be wrapped forwardly between patient's legs and detachably engaged to said at least one waist strap wrapped around the patient's torso.

12. The thoracic-lumbar-sacral corrective orthosis brace of claim 7, wherein said strap means further comprises at least one, seating engagement strap which extends outwardly from said side edge of said rigid back portion and which can be used to secure the patient wearing said brace in a chair having a back to prevent the patient from slumping or falling out of the chair by wrapping said seating engagement straps around the back of the chair.

13. The thoracic-lumbar-sacral corrective orthosis brace of claim 12 wherein said at least one seating engagement strap can be used as a chest engagement strap to aid in holding said rigid back portion against the patient's back.

14. The thoracic-lumbar-sacral corrective orthosis brace of claim 12, wherein said at least one seating engagement straps can be used as a grip by a person other than a patient in assisting the patient in walking.

15. The thoracic-lumbar-sacral corrective orthosis brace of claim 1, wherein said rigid back portion comprises a rigid central core covered at least on its front facing surface with a padding and covering material.

16. The thoracic-lumbar-sacral corrective orthosis brace of claim 1, wherein said strap means are detachably fixably to said rigid back portion.

17. A thoracic-lumbar-sacral corrective orthosis brace for supporting, controlling and correcting poor structural and postural curvature and deformities of the spine of a patient wearing the brace, comprising:

a generally concave, unitary, rigid back portion extending between a top and bottom edges, and extending between two side edges and having a front and rear facing surface, said rigid back portion being concavely curved rearwardly from said two side edges away from the patient's back, said top edge lying in the vicinity of approximately the number five thoracic vertebra and said bottom edge extending down to the sacrum thereof, said rigid back portion substantially overlying the patient's back;

a flexible vest portion which is detachably affixed to said concave, unitary, rigid back portion near its top edge, said concave rigid back portion having rigid back portion straps originating from its side edges, said rigid back portion straps comprising at least one waist strap which can be used to adjustably and detachably strap said concave rigid back portion to the patient's back to apply controlling and corrective pressure to the patient's spine between the vicinity of the number five thoracic vertebra and the sacrum, and at least one chair engaging strap to adjustably and detachably secure the concave rigid back portion to a chair, and at least one strap originating from said bottom edge of said concave rigid back portion which can be passed forwardly between the patient's legs and adjustably and detachably affixed to said waist strap wrapped around the patient's waist, said flexible vest portion being worn on the patient's upper torso and having chest overlaying portions which can be adjustably and detachably affixed to said waist strap wrapped around the patient's waist; and a lumbar support cushion located on said front facing surface of said concave rigid back portion, said lumbar support cushion being available in a variety of shapes, sizes and densities, wherein said brace is thus capable of being adjusted to fit the patient's torso and spinal condition as required.

18. A thoracic-lumbar-sacral corrective orthosis brace for supporting, controlling and correcting poor structural and postural curvature and deformations of the spine of a patient wearing the brace, comprising:

an arcuate, unitary, rigid back portion extending between top and bottom edges, and extending between two side edges and having a front and rear facing surface, said rigid back portion being curved generally rearwardly from said two side edges away from the patient's back, said top edge lying in the vicinity of approximately the number five thoracic vertebra and said bottom edge lying in the vicinity of the sacrum; and a flexible vest portion, said vest portion being attached to said arcuate, unitary, rigid back portion, said arcuate rigid back portion and said flexible vest portion having means with which to hold said arcuate rigid back portion against the patient's back to apply controlling and corrective pressure to the patient's spine between the vicinity of the number five thoracic vertebra and the sacrum thereof, wherein said means with which to hold said arcuate rigid back portion against the patient's back comprises at least one waist strap fixed to said arcuate rigid back portion which can be secured around the patient's torso and at least one portion of said flexible vest portion which can be detachably engaged with said at least one waist strap.

* * * * *